US009102604B1

(12) United States Patent
Rozov et al.

(10) Patent No.: US 9,102,604 B1
(45) Date of Patent: Aug. 11, 2015

(54) METHODS FOR CLEANING DISTILLING COLUMNS

(75) Inventors: Leonid A. Rozov, Fair Lawn, NJ (US); Linas Kudzma, Annandale, NJ (US); Hong-Chang Lee, Livingston, NJ (US); Ronald Bell, Glen Gardner, NJ (US)

(73) Assignees: BAXTER INTERNATIONAL INC., Deerfield, IL (US); BAXTER HEALTHCARE SA, Glattpark (Opfikon) (CH)

( * ) Notice: Subject to any disclaimer, the term of this patent is extended or adjusted under 35 U.S.C. 154(b) by 640 days.

(21) Appl. No.: 12/705,956

(22) Filed: Feb. 15, 2010

(51) Int. Cl.
*C07C 41/42* (2006.01)
*B01D 3/34* (2006.01)
*C23G 1/02* (2006.01)
*F28G 9/00* (2006.01)
*B08B 3/04* (2006.01)

(52) U.S. Cl.
CPC . *C07C 41/42* (2013.01); *B01D 3/34* (2013.01); *B08B 3/04* (2013.01); *C23G 1/02* (2013.01); *F28G 9/00* (2013.01); *Y10S 134/00* (2013.01); *Y10S 148/017* (2013.01)

(58) Field of Classification Search
CPC .......... B01D 3/34; C07C 41/34; C07C 41/36; C07C 41/42; C07C 41/46; C23G 1/02; C23G 1/04; C23G 1/14; C23G 1/16; C23F 14/02; C23F 17/00; C22F 1/10; C22C 19/05; F28G 9/00; B08B 3/04; B08B 3/106; B08B 7/0064; B08B 9/00; B08B 13/00; Y10S 148/017; Y10S 159/13; Y10S 159/15; Y10S 159/20; Y10S 202/01; Y10S 420/00; Y10S 134/00
See application file for complete search history.

(56) References Cited

U.S. PATENT DOCUMENTS

| | | | |
|---|---|---|---|
| 2,921,858 A | 1/1960 | Hall | |
| 2,992,276 A | 7/1961 | Weinmayr | |
| 3,440,170 A | 4/1969 | de Hek | |
| 3,667,487 A | 6/1972 | Schoenbeck et al. | |
| 4,250,334 A | 2/1981 | Coon et al. | |
| 4,432,808 A | 2/1984 | Heubusch | |
| 4,613,405 A | 9/1986 | Godbille | |
| 4,637,899 A | 1/1987 | Kennedy, Jr. | |
| 4,657,638 A | 4/1987 | le Grand et al. | |
| 5,502,249 A | 3/1996 | Fillers et al. | |
| 5,506,364 A | 4/1996 | Martin et al. | |
| 5,632,866 A * | 5/1997 | Grant | 203/12 |
| 5,679,576 A * | 10/1997 | Kawai et al. | 436/55 |
| 5,684,211 A | 11/1997 | Kawai et al. | |
| 5,811,596 A | 9/1998 | Kawai et al. | |
| 5,852,201 A | 12/1998 | Lenz et al. | |
| 5,969,193 A | 10/1999 | Terrell | |
| 5,990,176 A | 11/1999 | Bieniarz et al. | |
| 6,074,668 A | 6/2000 | Flament-Garcia et al. | |
| 6,083,514 A | 7/2000 | Chang et al. | |
| 6,162,443 A | 12/2000 | Flament-Garcia et al. | |
| 6,288,127 B1 | 9/2001 | Bieniarz et al. | |
| 6,444,859 B2 | 9/2002 | Bieniarz et al. | |
| 6,469,219 B1 | 10/2002 | Khrimian et al. | |
| 6,558,679 B2 | 5/2003 | Flament-Garcia et al. | |
| 6,677,492 B2 | 1/2004 | Bieniarz et al. | |
| 7,230,143 B2 | 6/2007 | Jones et al. | |
| 7,365,195 B2 * | 4/2008 | Lemmens et al. | 540/540 |
| 7,816,409 B2 | 10/2010 | Pacheco et al. | |
| 2003/0200963 A1 | 10/2003 | Flament-Garcia et al. | |
| 2004/0048932 A1 | 3/2004 | Bieniarz et al. | |
| 2004/0124076 A1 * | 7/2004 | Sharratt et al. | 203/59 |
| 2005/0113603 A1 | 5/2005 | Belmonte et al. | |
| 2006/0258755 A1 | 11/2006 | Terrell et al. | |
| 2009/0275785 A1 | 11/2009 | Jones et al. | |
| 2013/0046117 A1 * | 2/2013 | Kudzma et al. | 568/682 |

FOREIGN PATENT DOCUMENTS

| | | |
|---|---|---|
| EP | 0 199 288 | * 10/1986 |
| EP | 0380169 | 8/1990 |
| WO | WO-97/25303 A1 | 7/1997 |
| WO | 99/00474 | * 1/1999 |

OTHER PUBLICATIONS

Corrosion-Resistant Alloys. Haynes International Inc. Retrieved from the Internet on Nov. 3, 2009 URL<http://www.haynesintl.com/CRAlloys.htm>. Publicly available before Feb. 15, 2010.
Debold et al., How to passivate stainless steel parts, *Modern Machine Shop*, pp. 98-104 (Oct. 2003).
Fabrication of Hastelloy™ Corrosion-Resistant Alloys, General Guidelines. Haynes International Inc. (2003).
Frye et al., Nickel passivation in acidic chloride solution using optical second harmonic generation, *Chem. Mater.*, 2:246-8 (1990).
Goodloe® Structured Packing product sheet. Koch-Glitsch LP. Retrieved from the Internet on Nov. 3, 2009: <URL: <http://www.koch-ottoyork.com/products/Goodloe.htm>. Publicly available before Feb. 15, 2010.
Hastelloy® G-30® Alloy Technical Information. Haynes International, Kokomo, Indiana. Publicly available before Feb. 15, 2010.
Kolmetz et al., Optimize distillation column design for improved reliability in operation and maintenance, 2nd Best Practices in Process Plant Management conference, Kuala Lumpur, Malaysia (Mar. 14-15, 2005).
Roberts et al., Prevention and suppression of metal packing fires, *J. Hazardous Mater.*, 104:247-53 (2003).
Standard Practice for Cleaning, Descaling, and Passivation of Stainless Steel Parts, Equipment, and Systems, ASTM Designation A380-06 (May 2006).
Standard Specification for Chemical Passivation Treatments for Stainless Steel Parts, ASTM Designation A967-05 (Sep. 2005).

* cited by examiner

*Primary Examiner* — Virginia Manoharan
(74) *Attorney, Agent, or Firm* — Marshall, Gerstein & Borun LLP

(57) ABSTRACT

A method for cleaning a distilling column includes providing a distilling column including a packing containing nickel and adding hydrochloric acid to the distilling column to wash at least a portion of the packing, thereby cleaning the distilling column.

24 Claims, No Drawings

METHODS FOR CLEANING DISTILLING COLUMNS

BACKGROUND

1. Field of the Disclosure

The disclosure generally relates to methods for cleaning a distilling column comprising a metallic packing, and more particularly to methods for distilling sevoflurane.

2. Brief Description of Related Technology

It is well known that industrial equipment is susceptible to corrosion. Corrosion is a problem of particular importance for chemical processing equipment, for example, because corrosion salts can contaminate and/or otherwise negatively affect the purity and/or integrity of desired, isolated end products. Therefore, various strategies have been adopted to reduce and/or mitigate corrosion and the undesirable effects thereof on industrial metallic equipment.

For example, high performance nickel-based alloys which are deemed to be substantially resistant to corrosion can be used to construct the metal components of industrial equipment.

Additionally, periodic cleanings can be performed to remove corrosion salts from industrial metallic equipment. Acidic cleaning solutions are commonly employed to remove scale and rust from industrial process equipment such as boilers and heat exchangers. However, acid is corrosive to the metal components of the equipment. Therefore, as disclosed in U.S. Pat. No. 4,637,899, the acidic cleaning solutions can be formulated to include corrosion inhibitors to minimize the corrosive effect that the acid has on the equipment.

U.S. Patent Publication No. 2009/0275785 discloses removing reactive metal salts from the surface of metallic equipment used in the distillation of sevoflurane by contacting the interior surfaces of the equipment with an aqueous solution of a passivation agent which renders the non-inert surface of a metal, particularly stainless-steel, inert. Passivating involves the spontaneous formation of a chemically inactive film on the surface of metals such as stainless steel via exposure to air or other oxygen-containing environments. Exemplary passivation agents disclosed in U.S. Patent Publication No. 2009/0275785 include citric acid, nitric acid, and a mixture of nitric acid and sodium or potassium dichromate. Each of the foregoing passivation agents involves the utilization of a mild oxidant for the purpose of enhancing the spontaneous formation of the protective passive film.

SUMMARY

In one aspect, a method for cleaning a distilling column comprises providing a distilling column including a packing comprising nickel and adding hydrochloric acid to the distilling column to wash at least a portion of the packing, thereby cleaning the distilling column.

In a further aspect, a method for distilling sevoflurane comprises adding at least one sample containing sevoflurane to a distilling column, said distilling column including a packing comprising nickel, distilling the sample to obtain purified sevoflurane, washing at least a portion of the packing with hydrochloric acid, adding at least one additional sample containing sevoflurane to the distilling column, and distilling the additional sample to obtain additional purified sevoflurane.

DETAILED DESCRIPTION

Like other industrial metallic equipment, the present inventors unexpectedly found that packing comprising nickel, even though it is generally deemed to be resistant to corrosion, is susceptible to corrosion. The inventors recognized that the presence of corrosion salts in the packing of sevoflurane distillation systems can catalyze the decomposition of sevoflurane (1,1,1,3,3,3-hexafluoro-2-(fluoromethoxy)propane) to form impurities such as formaldehyde, 1,1,1,3,3,3-hexafluoro-isopropanol (HFIP), and hydrofluoric acid as shown, for example, in Scheme 1. The aforementioned decomposition pathway is believed to further accelerate the formation of additional corrosion salts in the packing of distillation systems because of the generation of (additional) hydrofluoric acid.

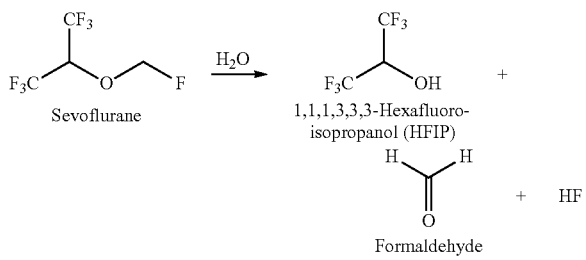

Scheme 1. Decomposition of Sevoflurane.

The present disclosure is directed to methods for cleaning a distillation column including a packing comprising nickel such that a significant portion of corrosion salts present in the packing are dissolved and can thereby be easily removed from the packing. The disclosed methods thus enable distillation columns to be off-line for relatively short maintenance periods. Accordingly, the disclosed methods facilitate the increased production of purified sevoflurane. Moreover, the disclosed methods enable the packing comprising nickel, which is expensive, to be reused rather than replaced.

In one aspect, a method for cleaning a distilling column comprises providing a distilling column including a packing comprising nickel and adding hydrochloric acid to the distilling column to wash at least a portion of the packing, thereby cleaning the distilling column.

In a further aspect, a method for distilling sevoflurane comprises adding at least one sample containing sevoflurane to a distilling column, said distilling column including a packing comprising nickel, distilling the sample to obtain purified sevoflurane, washing at least a portion of the packing with hydrochloric acid, adding at least one additional sample containing sevoflurane to the distilling column, and distilling the additional sample to obtain additional purified sevoflurane.

While the present disclosure expressly contemplates using metal packing not including nickel to fractionate a sample contained within the distillation column (for example, certain grades of stainless steels do not include any nickel at all), the packing generally comprises nickel as such packing demonstrates increased corrosion resistance and is thus more suitable for use in the methods of the disclosure. Suitable packings can be made from both nickel-containing alloys and substantially pure nickel. More specifically, suitable nickel-containing alloys typically comprise at least 30 weight percent nickel. Typically, the nickel-containing alloys further comprise molybdenum, chromium, cobalt, iron, or a combination thereof. Representative nickel-containing alloys that can be used to form the packing include but are not limited to HASTELLOY® corrosion-resistant alloys such as HASTELLOY® B-2 alloy, HASTELLOY® B-2 alloy, HASTEL- LOY® B-3 alloy, HASTELLOY® C-4 alloy, HASTELLOY® C-2000 alloy, HASTELLOY® C-22 alloy, HASTELLOY® C-276 alloy, HASTELLOY® G-30 alloy, HASTELLOY® N alloy, and HASTELLOY® W alloy (Haynes International, IN), MONEL® alloys such as MONEL® alloy 400 (Special Metals Corp., NY), INCONEL® alloys such as INCONEL® alloy 600 (Special Metals Corp., NY), and INCOLOY® alloys such as INCOLOY® alloy 800 (Special Metals Corp., NY). Representative substantially pure nickel materials that can be used to form the packing include but are not limited to Nickel 200 (Special Metals Corp., NY). Particularly suitable commercially available packings include GOODLOE® packings made from HASTELLOY® alloy (Koch-Otto York, TX).

Hydrochloric acid is used in the disclosed methods because it is particularly effective and efficient in cleaning the corrosion salts from packing comprising nickel. Moreover, hydrochloric acid is easier to handle and less expensive than other acids. The hydrochloric acid is generally used at a concentration between about 0.02 molar and about 0.50 molar, for example, between about 0.03 molar and about 0.30 molar, and/or at relatively low concentrations between about 0.05 molar and about 0.20 molar, for example about 0.05 molar, about 0.10 molar, about 0.15 molar, and/or about 0.20 molar.

The methods of the invention can include adding at least one sample containing (crude) sevoflurane to the distilling column and subsequently distilling the sample, using the packing comprising nickel to fractionate the sample and thereby obtain (relatively) purified sevoflurane. The distilling step can be performed before and/or after adding the hydrochloric acid to wash at least a portion of the packing. Typically, a quantity of hydrochloric acid which is sufficient to submerge a portion of the packing is added to the distilling column. If the packing is substantially contaminated with colored, deposited corrosion salts, the progress of the cleaning process can be monitored by visual inspection as the acidic solution will become colored after contacting the packing for a period of time. Typically, the packing is submerged under the acid for a period between about 10 minutes and about 24 hours, for example, between about 20 minutes and 8 hours, and/or between about 30 minutes and 4 hours. The period of time needed to cleanse the packing can be determined by analyzing the content of HFIP in the (relatively) purified sevoflurane distillate by gas chromatography, or by measuring (approximating) the acidity of the (relatively) purified sevoflurane distillate.

Analysis for hexafluoroisopropanol (HFIP) in sevoflurane can be performed on a capillary or packed gas chromatographic column of suitable length and diameter. Most typically, a packed gas chromatographic column about 4 meters in length and having an internal diameter of about 2.1 mm.

Acidity is measured by extracting the (relatively) purified sevoflurane distillate with water (in a 1:1 volume-to-volume ratio) and measuring the acidity of the resulting water.

If the HFIP and/or HF (acidity) contents (measurements) of a purified sevoflurane distillate obtained from a sample containing (crude) sevoflurane exceed selected threshold levels after the packing is cleaned/contacted with the acid for a period of time, then additional cleaning of the packing is needed.

Similarly, the HFIP and/or HF (acidity) contents (measurements) of purified sevoflurane distillate can be monitored to determine when it is appropriate to wash the packing as disclosed herein. If unacceptable levels of HFIP or acidity are demonstrated, the washing step should be performed to reduce decomposition of sevoflurane in the distillation apparatus.

After submerging the packing with the acid, the acid can be drained from the distilling column. A quantity of base may then optionally be added to the distilling column (after the washing step) to submerge/contact a portion (or preferably all) of the packing previously contacted with the acid and thereby neutralize any residual acid in the distillation system in order to return the distillation system to a normal state. A moderate base such as 1-10 wt. % sodium carbonate solution is particularly suitable for this purpose, but any base can be used for the neutralization step. After submerging/contacting the packing and the interior of the distilling column for a brief period of time, the base can then be drained from the distilling column.

Instead of, or in addition to, adding abuse to neutralize any residual acid, water can be added to the distilling column (after the washing step) to submerge/contact a portion or preferably all) of the packing previously contacted with the acid (and base, if used) so as to rinse the distilling column and packing so as to remove any residual chemicals therefrom. After submerging/contacting the packing and the interior of the distilling column for a brief period of time, the water can then be drained from the distilling column. The pH of the drained water can be analyzed to determine whether it is still acidic, and if so, additional water can be added to continue rinsing the distilling column and packing material so as to remove any residual chemicals therefrom until the pH of the water gives a neutral reading (e.g., between 5.0 and 7.50).

The following example is provided to illustrate the disclosure, but is not intended to limit the scope thereof.

Example 1

Washing of Distilling Column Packing Contaminated with a Green Deposit

A portion of contaminated packing (GOODLOE® packing made from HASTELLOY® alloy) was cut from a roll that had been removed from a sevoflurane distilling column. The packing was contaminated with a green deposit with some white inclusions.

The contaminated packing was placed in a glass beaker and treated for approximately one hour with 0.5 L of 0.1 M hydrochloric acid. The resulting greenish-bluish acid solution was decanted and the packing was washed with running tap water for approximately 10 minutes. The packing was then contacted with 2 wt. % sodium carbonate solution for approximately one hour, washed again for approximately 10 minutes with running water, and air dried overnight. The procedure dramatically changed the appearance of the packing: from gray/green with some white inclusions to shiny silver without any traces of inclusions.

A water-saturated sample of sevoflurane and a small amount of the freshly cleaned Hastelloy packing were charged into a two-neck 0.5 L PYREX® round-bottom flask. An 18"×¾" glass vacuum-jacketed column filled with small pieces of the freshly cleaned packing was topped with a reflux condenser kept at 5° C., and that assembly was attached to the round-bottom flask. The sample of sevoflurane was refluxed for seven days. One-milliliter samples were taken after the 1st, 3rd, 6th, and 7th days of reflux and analyzed by gas chromatography. No increases in HFIP or other impurities were observed.

In contrast, increases in HFIP and other impurities (such as HF, as demonstrated by increased acidity) were observed when the same experiment was performed using contaminated packing (in both the two-neck round bottom flask and the vacuum-jacketed column).

Therefore, this example demonstrates that adding hydrochloric acid to a distilling column to wash at least a portion of the packing contained therein is effective in cleaning the distilling column to remove salts which catalyze the decomposition of sevoflurane even after a prolonged heating.

Numerous modifications and variations of the method for cleaning a distilling column described herein are expected to occur to those skilled in the art in view of the accompanying disclosure. Consequently, only such limitations as appear in the appended claims should be placed on the invention.

What is claimed is:

1. A method for cleaning a distilling column comprising:
providing a distilling column including a packing comprising nickel;
adding hydrochloric acid to the distilling column to wash at least a portion of the packing, thereby cleaning the distilling column; and,
distilling at least one sample containing sevoflurane in the distilling column before adding the hydrochloric acid.

2. The method according to claim 1, wherein the packing comprises a nickel-containing alloy.

3. The method according to claim 1, wherein the packing comprises at least 30 weight percent nickel.

4. The method according to claim 1, wherein the packing comprises a nickel containing alloy comprising at least one element selected from the group consisting of molybdenum, chromium, cobalt, and iron.

5. The method according to claim 1, wherein the packing comprises nickel metal.

6. The method according to claim 1, wherein the hydrochloric acid has a concentration between about 0.02 molar and about 0.50 molar.

7. The method according to claim 1, wherein the hydrochloric acid has a concentration between about 0.03 molar and about 0.30 molar.

8. The method according to claim 1, wherein the hydrochloric acid has a concentration between about 0.05 molar and about 0.20 molar.

9. A method for cleaning a distilling column comprising:
providing a distilling column including a packing comprising nickel;
adding hydrochloric acid to the distilling column to wash at least a portion of the packing, thereby cleaning the distilling column; and,
distilling at least one sample containing sevoflurane in the distilling column after adding the hydrochloric acid.

10. A method for distilling sevoflurane comprising:
adding at least one sample containing sevoflurane to a distilling column, said distilling column including a packing comprising nickel;
distilling the sample to obtain purified sevoflurane;
washing at least a portion of the packing with hydrochloric acid;
adding at least one additional sample containing sevoflurane to the distilling column; and,
distilling the additional sample to obtain additional purified sevoflurane.

11. The method according to claim 10, wherein the washing includes adding to the distilling column a quantity of the hydrochloric acid sufficient to submerge a portion of the packing.

12. The method according to claim 11, further comprising draining the acid from the distilling column.

13. The method according to claim 12, further comprising adding a base to the distilling column after the washing step.

14. The method according to claim 13, further comprising adding to the distilling column a quantity of water sufficient to submerge the portion of the packing after the washing step.

15. The method according to claim 14, further comprising draining the water, and adding additional water to the distilling column when the drained water is acidic.

16. The method according to claim 10, wherein the washing step is performed after analysis of the purified sevoflurane demonstrates unacceptable levels of at least one of hexafluoroisopropanol and acidity.

17. The method according to claim 10, wherein the packing is contaminated with deposits prior to the washing step.

18. The method according to claim 10, wherein the packing comprises a nickel-containing alloy.

19. The method according to claim 10, wherein the packing comprises at least 30 weight percent nickel.

20. The method according to claim 10, wherein the packing comprises a nickel containing alloy comprising at least one element selected from the group consisting of molybdenum, chromium, cobalt, and iron.

21. The method according to claim 10, wherein the packing comprises nickel metal.

22. The method according to claim 10, wherein the hydrochloric acid has a concentration between about 0.02 molar and about 0.50 molar.

23. The method according to claim 10, wherein the hydrochloric acid has a concentration between about 0.03 molar and about 0.30 molar.

24. The method according to claim 10, wherein the hydrochloric acid has a concentration between about 0.05 molar and about 0.20 molar.

* * * * *